United States Patent
Xue et al.

(10) Patent No.: US 10,309,977 B2
(45) Date of Patent: Jun. 4, 2019

(54) DEVICE FOR DETECTING AND/OR ANALYZING BIO-CHIP

(71) Applicant: CapitalBio Corporation, Beijing (CN)

(72) Inventors: Yuan Xue, Beijing (CN); Guanbin Zhang, Beijing (CN); Cheng Chen, Beijing (CN); Kaijun Zhao, Beijing (CN); Yu Dong, Beijing (CN); Jing Cheng, Beijing (CN)

(73) Assignee: CapitalBio Corporation, Beijing (CN)

( * ) Notice: Subject to any disclaimer, the term of this patent is extended or adjusted under 35 U.S.C. 154(b) by 51 days.

(21) Appl. No.: 15/511,216

(22) PCT Filed: Sep. 25, 2015

(86) PCT No.: PCT/CN2015/000661
§ 371 (c)(1),
(2) Date: Mar. 14, 2017

(87) PCT Pub. No.: WO2016/045234
PCT Pub. Date: Mar. 31, 2016

(65) Prior Publication Data
US 2017/0285050 A1    Oct. 5, 2017

(30) Foreign Application Priority Data
Sep. 28, 2014 (CN) .......................... 2014 1 0508609

(51) Int. Cl.
*G01N 35/00* (2006.01)
*G01N 21/25* (2006.01)
(Continued)

(52) U.S. Cl.
CPC ....... *G01N 35/00069* (2013.01); *G01N 21/15* (2013.01); *G01N 21/251* (2013.01);
(Continued)

(58) Field of Classification Search
CPC ........ A61B 17/00491; A61B 17/12186; A61B 17/12195; A61B 18/1477;
(Continued)

(56) References Cited

U.S. PATENT DOCUMENTS 6,333,007 B1 * 12/2001 Svensson ............ B01F 11/0266
422/404
7,663,750 B2 * 2/2010 Bahatt ................ G01N 21/0332
356/328
(Continued)

FOREIGN PATENT DOCUMENTS

CN    1288516 A    3/2001
CN    1311436 A    9/2001
(Continued)

OTHER PUBLICATIONS

European Patent Office, Extended European Search Report for Application No. EP 15844745.8, dated May 9, 2018, 9 pages.
(Continued)

*Primary Examiner* — Jennifer Wecker
(74) *Attorney, Agent, or Firm* — Rimon, P.C.

(57) ABSTRACT

In some aspects, the present disclosure provides a biochip detecting device that comprises a first shell (2) connect to a second shell (1), and a rotatable support frame (5) of biochip possessing a detecting zone that holds one or more biochips, and a detector (7).

28 Claims, 4 Drawing Sheets

(51) Int. Cl.
*G01N 21/15* (2006.01)
*G01N 21/78* (2006.01)
*G01N 1/10* (2006.01)
*G01N 21/88* (2006.01)
*G01N 35/02* (2006.01)
*G01N 15/14* (2006.01)
*B01L 3/00* (2006.01)

(52) U.S. Cl.
CPC ............ *G01N 21/78* (2013.01); *B01L 3/5027* (2013.01); *B01L 2200/10* (2013.01); *G01N 15/1436* (2013.01); *G01N 21/88* (2013.01); *G01N 35/025* (2013.01); *G01N 2035/00158* (2013.01); *G01N 2035/00306* (2013.01)

(58) Field of Classification Search
CPC ...... A61B 2017/005; A61B 2017/1205; A61B 2018/00589; A61B 2018/00601
See application file for complete search history.

(56) References Cited

U.S. PATENT DOCUMENTS

| | | |
|---|---|---|
| 2005/0095172 A1 | 5/2005 | Nagaoka et al. |
| 2007/0048789 A1 | 3/2007 | Truex et al. |
| 2011/0051133 A1 | 3/2011 | Ogawa |
| 2011/0090490 A1* | 4/2011 | Ogawa ............... G01N 21/15 356/237.2 |
| 2011/0294139 A1* | 12/2011 | Takeda ............... G01N 15/1484 435/7.1 |
| 2012/0053068 A1* | 3/2012 | Remacle ............. C12Q 1/6851 506/9 |
| 2013/0164175 A1 | 6/2013 | Kim et al. |
| 2014/0063498 A1* | 3/2014 | Numao ................. G08B 17/10 356/338 |

FOREIGN PATENT DOCUMENTS

| | | |
|---|---|---|
| CN | 102004159 A | 4/2011 |
| CN | 102042957 A | 5/2011 |
| CN | 104237544 A | 12/2014 |
| EP | 1584917 A2 | 10/2005 |

OTHER PUBLICATIONS

The International Bureau of WIPO, International Preliminary Report on Patentability for Int'l Application No. PCT/CN2015/000661, dated Mar. 28, 2017, 1 page.

State Intellectual Property Office of the P.R. China, International Search Report for Int'l Application No. PCT/CN2015/000661, dated Dec. 18, 2015, 3 pages.

State Intellectual Property Office of the P.R. China, Written Opinion of the International Searching Authority, dated Dec. 18, 2015, 6 pages.

European Patent Office, Office action response to European patent application 15844745.8, dated Dec. 6, 2018, 12 pages.

* cited by examiner

DEVICE FOR DETECTING AND/OR ANALYZING BIO-CHIP

CROSS-REFERENCE TO RELATED APPLICATIONS

This application is a U.S. National Phase of International Patent Application No. PCT/CN2015/000661, filed Sep. 25, 2015, which claims priority to Chinese Patent Application No. 201410508609.X, filed on Sep. 28, 2014, published as CN 104237544 A on Dec. 24, 2014, and the content of each application is incorporated by reference herein in its entirety for all purposes.

TECHNICAL FIELD

The present disclosure relates to the area of biochemistry and biotechnology. In particular, it is related to a device for detecting and/or analyzing a chip such as a biochip, and a method of using the device for detection and/or analysis.

BACKGROUND

With economic society's fleet development during the past decade, the need of all kinds of detectors is rapidly increasing. Meanwhile, breakthroughs in the field of material science, processing technology and microelectronics pushed the pace of bio-chip detecting study to a brand new stage. The application of bio-chip detection has drawn lots of attention, because of its ability to handle small volume of samples and/or reagents, low consumption of samples and reagents, its ability to control fluids, high integration level, and fast analytical speed. It has been widely applied to the biology, medicine and chemistry areas.

However, the present traditional bio-chip detectors and detecting devices that focus on a variety of physiological indexes such as blood fat and cholesterol generally have complicated structures. Their bulky volume and have high power consumption characteristics, plus their high prices, often increase the cost of bio-chip tests, which is not advantageous for common and personal biochemical detection.

Hence, a key issue need to be solved is how to provide bio-chip detectors that are portable and inexpensive.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, provided herein is a device, comprising: a first shell; a second shell connected to the first shell, and the first and second shells are capable of engaging each other to form a substantially closed carton; a rotatable support frame located between the first and second shells, and the rotatable support frame comprises a detecting zone that is capable of holding an object to be detected and/or analyzed; and a detector. In one embodiment, the first shell comprises a holding cavity. In one embodiment, the holding cavity comprises an upper plate facing the second shell. In another embodiment, the rotatable support frame is disposed on the upper plate of the holding cavity of the first shell. In some aspects, the upper plate comprises a through-hole that is capable of aligning with the detecting zone of the rotatable support frame.

In one embodiment, the device further comprises a light source. In some embodiments, the light source is disposed on the first shell or the second shell. In other embodiments, the light source and the detector are disposed on opposite sides of the rotatable support frame.

In another aspect, the object to be detected and/or analyzed by a device disclosed herein comprises a chip such as a biochip. In one embodiment, the device is for detecting and/or analyzing a chip such as a biochip. In one embodiment, the rotatable support frame comprises a plurality of detecting zones each of which is capable of holding an object to be detected and/or analyzed.

In one embodiment, the device further comprises an output unit for outputting a result of the detection and/or analysis. In one embodiment, the output unit is disposed on the first shell, such as in a holding cavity of the first shell. In another embodiment, the light source is disposed on the second shell. In one embodiment, the detector is disposed in the holding cavity of the first shell and aligns with the through-hole. In one embodiment, the detector, the light source, the detecting zone, and the through-hole are collinear when the first and second shells engage each other to form a substantially closed carton. In some embodiments, the first and second shells engage each other to form a closed carton.

In one aspect, a substantially closed carton disclosed herein means that the carton is closed such that the detection and/or analysis inside the carton is not affected by an outside environmental factor, for example, light or temperature. In some embodiments, the carton is substantially closed when the detection and/or analysis results are less than about 20%, less than about 15%, less than about 10%, less than about 5%, less than about 2%, less than about 1%, less than about 0.5%, or less than about 0.1% different compared to results when the carton is completely closed.

In one aspect, the device further comprises one or more macro lenses. In one embodiment, the one or more macro lenses are disposed in the holding cavity of the first shell. In one embodiment, the one or more macro lenses are disposed between the through-hole and the detector. In another embodiment, the one or more macro lenses are collinear with the through-hole and the detector.

In another aspect, the device further comprises one or more optical filters disposed between the through-hole and the one or more macro lenses.

In one embodiment, the device further comprises a rotary shaft disposed on or connected to the upper plate of the holding cavity of the first shell. In one embodiment, the rotary shaft is disposed on or connected to the support frame.

In one embodiment, the device further comprises a driving unit that is capable of rotating the rotary shaft. In one embodiment, the driving unit is disposed in the holding cavity.

In some embodiments, the driving unit comprises: a rotor connected to the rotary shaft, which rotor comprises a plurality of protuberances around the periphery of the rotor; a pushrod that is capable of applying a force to drive the rotation of the rotor, which pushrod is configured to fit the protuberances of the rotor and protrude from the holding cavity; a biasing member connected to the pushrod that is capable of resetting the position of the pushrod to release the rotor; a rotor securing lever that is connected to the lower surface of the upper plate of the holding cavity, which rotor securing lever comprises a neck that is capable of fitting the protuberances of the rotor to make the rotor spin in a single direction; and a spring connected to the rotor securing lever at one end and to the lower surface of the upper plate of the holding cavity at the other end.

In one embodiment, the pushrod comprises: a positioning rod disposed on the lower surface of the upper plate of the holding cavity; a guiding rod comprising a sharp-edged tip capable of fittingly engage the protuberances of the rotor, and a chute capable of fittingly engage the positioning rod, which guiding rod is connected to the biasing member; and a button connected to the guiding rod at one end, with the other end protruding from the holding cavity.

In one embodiment, the driving unit further comprises a damper connected to the rotor. In one embodiment, the device further comprises a light source and a shielding plate disposed at the periphery of the light source.

In another aspect, disclosed herein is a method of detecting and/or analyzing an object, comprising placing the object in the detecting zone of a device of the present disclosure.

DETAILED DESCRIPTION

Figure 1:
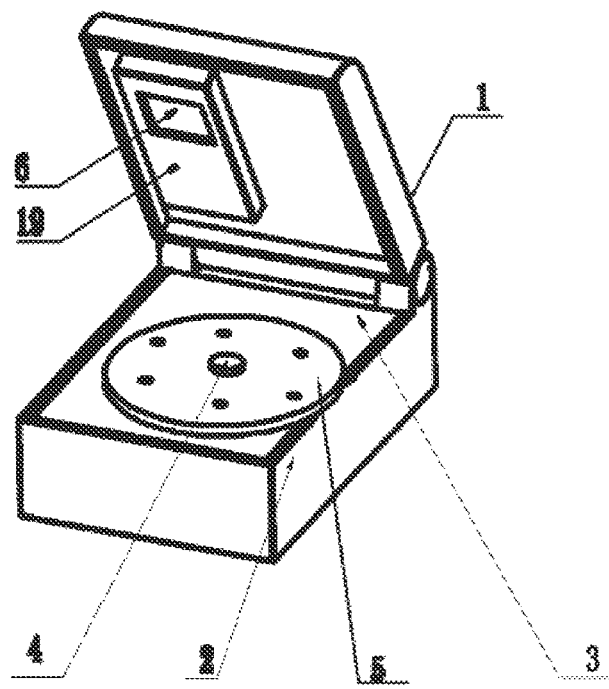
FIG. 1 is a structural diagram showing the structure of a bio-chip detector according to one aspect the present disclosure.
Figure 2:
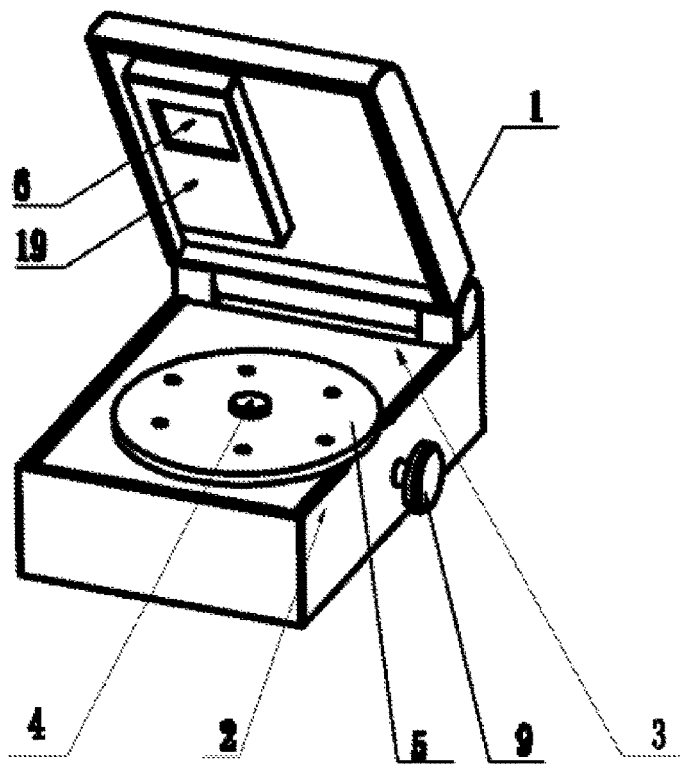
FIG. 2 is a structural diagram showing the structure of a bio-chip detector according to one aspect the present disclosure.
Figure 3:
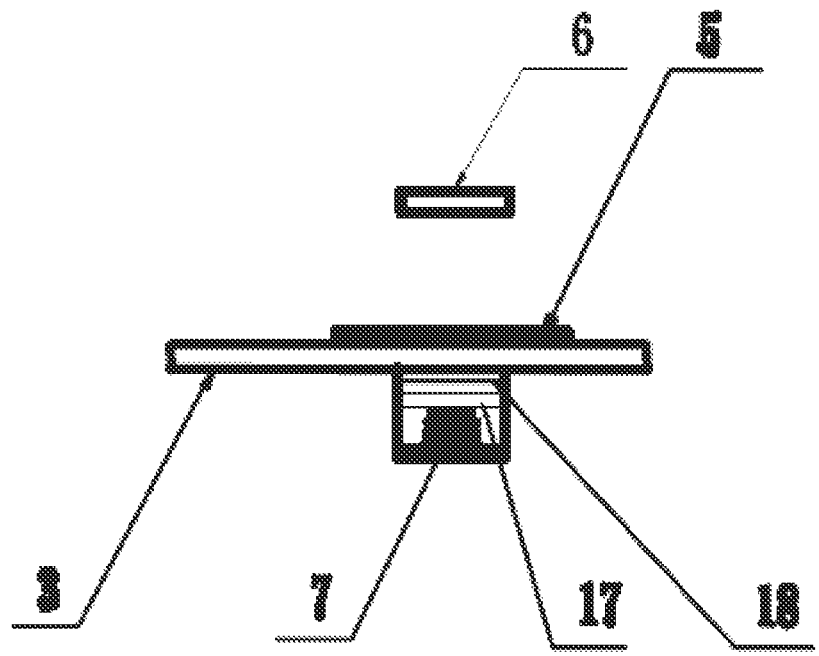
FIG. 3 is a view showing the partial structure of a bio-chip detector according to one aspect the present disclosure.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

As used herein, the singular forms "a", "an", and "the" include plural references unless indicated otherwise. For example, "an" object includes one or more objects.

It is understood that aspects and embodiments of the disclosure described herein include "consisting" and/or "consisting essentially of" aspects and embodiments.

Other objects, advantages and features of the present disclosure will become apparent from the following specification taken in conjunction with the accompanying drawings.

The present disclosure provides a biochip detecting device that comprises a first shell with a holding cavity, which first shell is connected with a second shell. In one aspect, the upper plate of the holding cavity faces the second shell. In one aspect, the device further comprises a rotatable support frame of biochip possessing a detecting zone that holds biochips. In one aspect, the support frame is set on the upper plate, and the upper plate also has a though-hole that can face the detecting zone. In another aspect, the device further comprises a light source that provides light for biochips, and the light source can be set either in the first shell or the second shell. In one aspect, the device further comprises a biochip detector that detects the testing zone of the biochip, and the detector is placed in either the first shell or the second shell depending on the side on which the light source is located. In one aspect, the detector and the light source are set on opposite sides of the support frame. In one aspect, the device further comprises a device which outputs the detection results, and the output device or unit is fixed in the holding cavity of the first shell. In one aspect, a biochip can be first placed on the biochip support frame. Then the testing zone can be exposed underneath the though-hole to permit the testing operation of the biochip detector, and the light source can be utilized based on demand. In one aspect, the device has features like structural simplicity, relative small volume, and great portability that permits outdoor operation in remote area with limited access to biotech, extending the range of application.

In one aspect, disclosed herein is a biochip detecting device that comprises all or some of the following components:

Two connected shells—a first shell and a second shell, and the first shell has a holding cavity, and the upper plate of the holding cavity faces the second shell.

A rotatable support frame—the support frame possesses a detecting zone that holds biochips, and is set on the upper plate, and the upper plate also has a through-hole that can face the detecting zone.

A light source—the light source provides lighting for biochips that is set either in the first shell or the second shell.

A biochip detector—the detector detects the testing zone of the biochip is placed in either the first shell or the second shell depending on the side on which the light source is located. In one aspect, the detector and the light source are set on opposite sides of the support frame.

An output unit or device—the device outputs the detection results and is fixed in the holding cavity of the first shell.

In one aspect, the light source can be placed on the second shell, and the biochip detector can be placed in the holding cavity of the first shell facing the through-hole.

In one aspect, the biochip detecting device also comprises one or more macro lenses that are fixed in the holding cavity of the first shell, and the macro lenses face the through-hole, set between the through-hole and the detector.

In one aspect, the biochip detecting device also comprises an optical filter that is set between the through-hole and the macro lenses.

In one aspect, the biochip detecting device also comprises a rotary shaft that is set on the upper plate of the holding cavity of the first shell, and the biochip support frame is fixed on the rotary shaft.

In one aspect, the biochip detecting device also comprises a driving device that is used to rotate the rotary shaft, and the driving device is fixed in the holding cavity.

In one aspect, the driving device comprises:

A rotor that is connected to the rotary shaft, and there are multiple protuberances around the periphery of the rotor;

As the subassembly to apply force to drive the rotation of the rotor, a pushrod that is designed to fit the protuberances of rotor, and the pushrod protrudes from the holding cavity;

A biasing member connected to the pushrod that resets the position of the pushrod to release the rotor;

A rotor securing lever that is connected to the lower surface of the upper plate of the holding cavity, and this lever has a neck that can fit the protuberances of rotor to make the rotor spin in a single direction;

A spring that is connected to the rotor securing lever at its one end and the lower surface of the upper plate of the holding cavity at the other end.

In one aspect, the pushrod comprises:

A positioning rod that is fixed on the lower surface of the upper plate of the holding cavity;

A guiding rod with a sharp-edged tip fitted to the protuberances of the rotor that has a chute that fits with the positioning rod, and this guiding rod is connected to the biasing member;

A button that is connected to the guiding rod at its one end, the other end of which protrudes from the holding cavity.

In one aspect, the device disclosed herein also comprises a damper connected to the rotor.

In one aspect, the device disclosed herein also comprises a shielding plate disposed at the periphery of the light source.

Also provided herein is a method of detecting and/or analyzing an object, comprising placing the object in the detecting zone of the device of any of the preceding embodiments.

In one aspect, the present disclosure provides a biochip detecting device featuring a simplified structure, reduced volume, and great portability.

Features of the presently disclosed methods and device are described herein with reference to the drawings. As shown in FIGS. 1-8, in some aspects, the present disclosure provides a type of biochip detecting device comprising a first shell (e.g., 2 in FIG. 1 or FIG. 2) connected to a second shell (e.g., 1 in FIG. 1 or FIG. 2). In one embodiment, the first shell is hingely joined to the second shell. In another aspect, the device further comprises a support frame (e.g., 5 in FIG. 1 or FIG. 2). In some embodiments, the support frame is a rotatable biochip support frame. In another aspect, the device further comprises a light source (e.g., 6 in FIG. 1 or FIG. 2). In yet another aspect, the device further comprises a detector (e.g., 7 in FIG. 3). In still another aspect, the device further comprises a detection result output device.

In one aspect, the first shell comprises a holding cavity. In some embodiments, the first shell comprises a carton body structure comprising an upper plate (e.g., 3 in FIG. 1 or FIG. 2). In one embodiment, the second shell comprises a carton cover structure, for example, one that is configured to interlock with the carton body structure of the first shell to form a closed system. In one aspect, the closed system is a controllably closed system, and the carton cover structure can be controlled to engage the carton body structure (to close the system) and/or to disengage the carton body structure (to open the system). In some embodiments, the controlling of the closing and/or opening of the system is automated. In other embodiments, the controllably closed system avoids or reduces influences on the detection structures and/or reactions in the device by external factors, such as contamination or environmental temperature fluctuation.

In one aspect, the support frame (such as a rotatable support frame of biochip) is set on the upper plate of the first shell. In some embodiments, the support frame comprises a detecting region. In specific embodiments, the detection region comprises a plurality of detecting zones, each of which is capable of holding an object to be analyzed and/or detected, such as a biochip. In some embodiments, the support frame comprises between about 1 and about 5, about 5 and about 10, about 10 and about 50, about 50 and about 100, or more than about 100 detecting zones. The detecting zones can be of the same or different size or shape. In addition, the same or different types of chips such as biochips can be installed on the plurality of detecting zones. In some embodiments, the device disclosed herein enables the detection of a plurality of the same or different substances, each on one of the plurality of detecting zones.

In some embodiments, a rotary shaft (e.g., 4 in FIG. 1 or FIG. 2) is set on the upper plate in the holding cavity of the first shell, on which the biochip support frame is fixed. In some embodiments, the upper plate comprises a through-hole (e.g., 8 in FIG. 4) capable of facing a detecting zone of the detection region. During the detecting process, in some aspects, the detection region can be adjusted so that a detecting zone (e.g., with a biochip installed on the detecting zone) faces the through-hole, by rotating the biochip support frame around the rotary shaft. This way, the detector can start detecting and/or analyzing the biochip through the through-hole. The biochip that is mounted on the support frame rotates with the support frame.

To provide light for the detection and/or analysis of a biochip and the reaction(s) on the biochip, in some embodiments, a light source is provided. Any suitable light source can be used, for example, a laser beam or a light-emitting diode (LED). In some embodiments, the light source is a lamp or natural light. When the light source is an ordinary lamp bead, the light source irradiates the biochip, in which a chromogenic reaction (such as a biochemical reaction) can be detected by the detector which receives information from the biochip to complete the detecting process. In some embodiments, the detector is used to detect the information on the portion of the biochip that requires testing. In some embodiments, the detector is set on either the first shell or the second shell, while the light source is set on the other shell so that the detector and the light source are on different sides of the biochip.

In one aspect, the detection result output device is wired or wireless. In some embodiments, the output device is mounted in the holding cavity of the first shell. In some embodiments, the wireless output device is based on Bluetooth. In other embodiments, the wired output device comprises a USB portal. Any suitable output device can be used, depending on the needs.

In one aspect, a biochip is placed on the support frame with the testing zone facing the through-hole for this device to work, and the detector detects and/or analyzes the testing portion of the biochip. In another aspect, the light source is utilized on demand. For example, the light source can be turned on, either manually or automatically, when the detection and/or analysis starts. In one aspect, the detection and/or analysis of a sample in the biochip (for example, a biomass, a tissue, a cell, a virus, a molecular complex, or a biological molecule) requires the light source and detector to be collinear. In some aspects, a device disclosed herein has structural simplicity, relative small volume, and great portability that permits outdoor operation in remote areas with limited access to biotech, thereby extending the scope of application.

In one aspect, the light source is set or mounted on the second shell, with the detector set or mounted in the holding cavity of the second shell, and the detector faces the through-hole. In some aspects, because the first shell and the second shell are hingely joined, the first and second shells can engage each other, for example, to form a sealed casing that ensures that the light source is simultaneously collinear with the detector and with the testing zone of the biochip, when two shells are buckled to form a carton. The positions of the light source and the detector are interchangeable.

In a further aspect, to avoid using optical apparatus based on lens optical path, a biochip detector provided in the present disclosure comprises a macro lens (e.g., 17 in FIG. 3) facing the through-hole and fixed in the holding cavity of the first shell. In specific embodiments, the macro lens is disposed between the detector and the through-hole of the upper plate. In certain embodiments, the macro lens magnifies objects (e.g., a sample in the biochip) to achieve the purpose of detecting microscopic samples. In one aspect, an apparatus of a small volume, such as a macro lens, is used to amplify an object to be detected and/or analyzed. In one embodiment, the macro lens may be in the form of optical lens combination or combinations to obtain higher magnification.

In another aspect, the device disclosed herein comprises an optical filter (e.g., 18 in FIG. 3) disposed between the through-hole and the macro lens. This device can be used to test chromogenic biochemical reactions when the light source is a common light source; however, when detection by different wavelengths is required, one or more optical filters can be used to filter a light source in order to obtain light with a desired wavelength or within a desired wavelength range. For example, when the test substance comprises a nucleic acid, the optical filter can be used to obtain light of 260 nm wavelength for the detection of nucleic acids.

Besides testing biological reactions, this device can also be used in many other fields, such as cell counting and/or sorting. In some aspects, a sample in a unit of a biochip can comprise one or more biological substances, for example, nucleic acids, proteins, lipids, and carbohydrates, and detection and/or analysis of the different biological substances within the sample can be conducted simultaneously or sequentially, using different indexes such as light of different wavelengths. Any chemical or biological reactions that are suitable for detection and/or analysis using a chip are within the scope of present disclosure.

Figure 4:
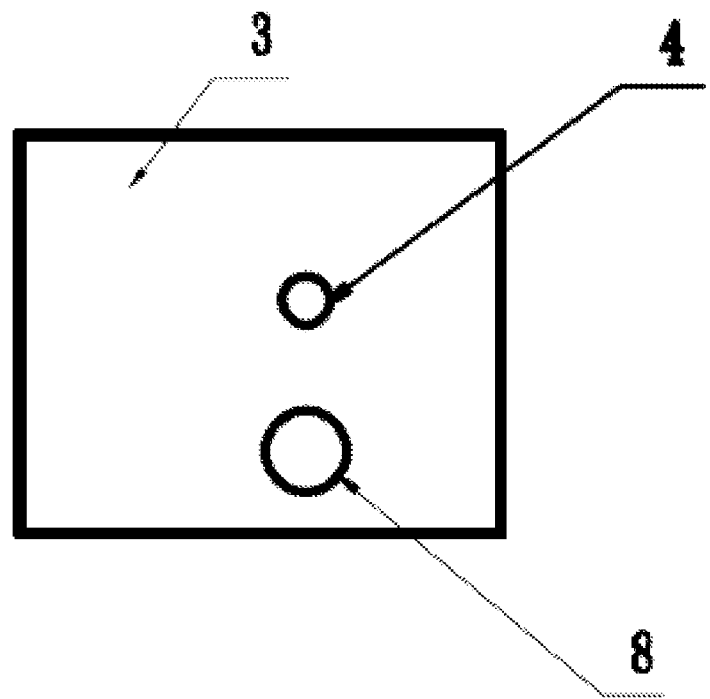
FIG. 4 is a view showing the upper plate structure of a bio-chip detector according to one aspect the present disclosure.
Figure 5:
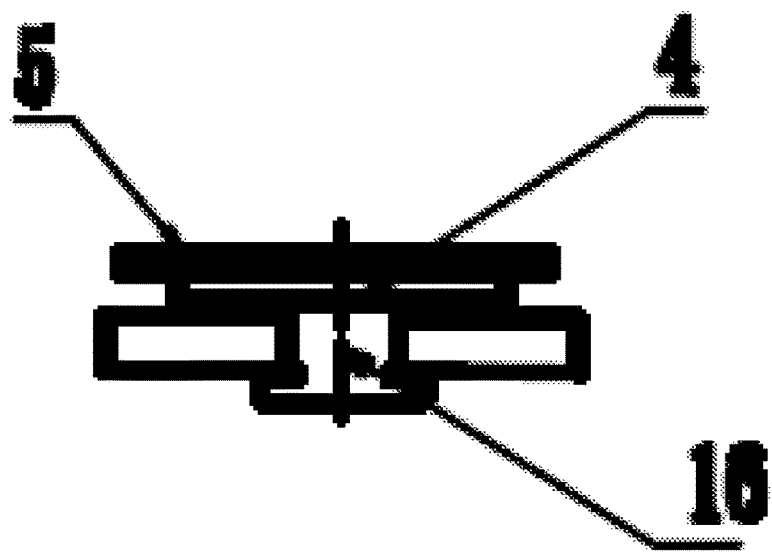
FIG. 5 is a view showing the rotating shaft connection structure of a bio-chip detector according to one aspect the present disclosure.

In a further embodiment, a device disclosed herein comprises a rotary shaft (e.g., 4 in FIG. 1 or FIG. 2) set on the upper plate in the holding cavity of the first shell, on which the biochip support frame is fixed. In one aspect, the rotary shaft is connected to the support frame, and synchronous rotation of the rotary shaft and the support frame is achieved by the rotation of the rotary shaft around its own axis. In one aspect, rotation of the support frame around the axis of the rotary shaft exposes different testing zones of the support frame (and the chips placed on the testing zones) to the through-holes of the upper plate (e.g., through-hole 8 of upper plate 3 as shown in FIG. 4) for detection and/or analysis of the chip, or detection and/or analysis at different locations of a chip. In one aspect, the support frame is fixed to the rotary shaft, and the support frame and the rotary shaft rotates as a whole relative to the upper plate. Alternatively, the rotary shaft is a relatively fixed structure with the upper plate (e.g., the upper plate and the rotary shaft rotates as a whole), while the support frame can rotate around the rotary shaft. In any of the preceding embodiments, bearing junction can be used to realize the rotation of the support frame relative to the upper plate. A bearing can comprise a rotating axle and a linearly moving shaft.

In still another aspect, a device disclosed herein comprises a driving device that actuates the rotary shaft. In one embodiment, the driving device is set in the holding cavity of the first shell. In one aspect, the driving device comprises a motor such as a stepping motor.

Figure 6:
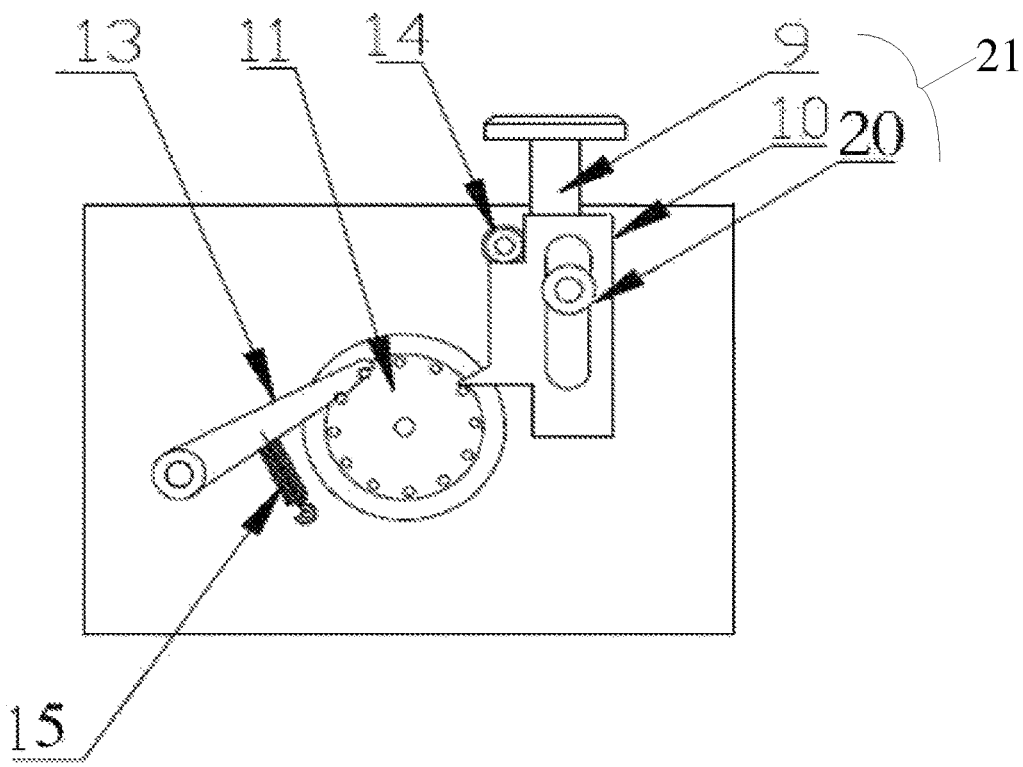
FIG. 6 is a view showing the driver structure of a bio-chip detector according to one aspect the present disclosure.
Figure 7:
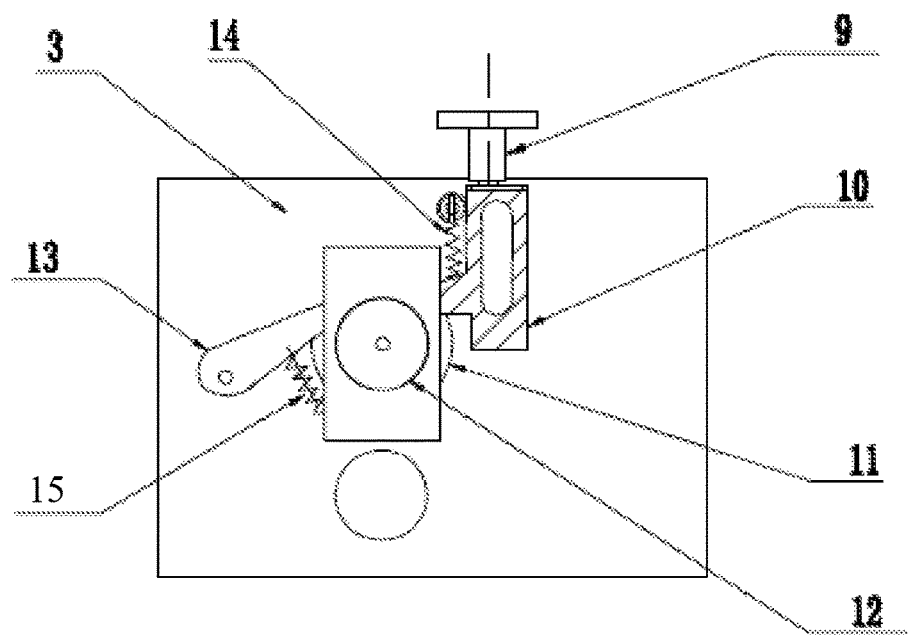
FIG. 7 is a structural diagram of a driver structure fixed to a damper of a bio-chip detector according to one aspect the present disclosure.
Figure 8:
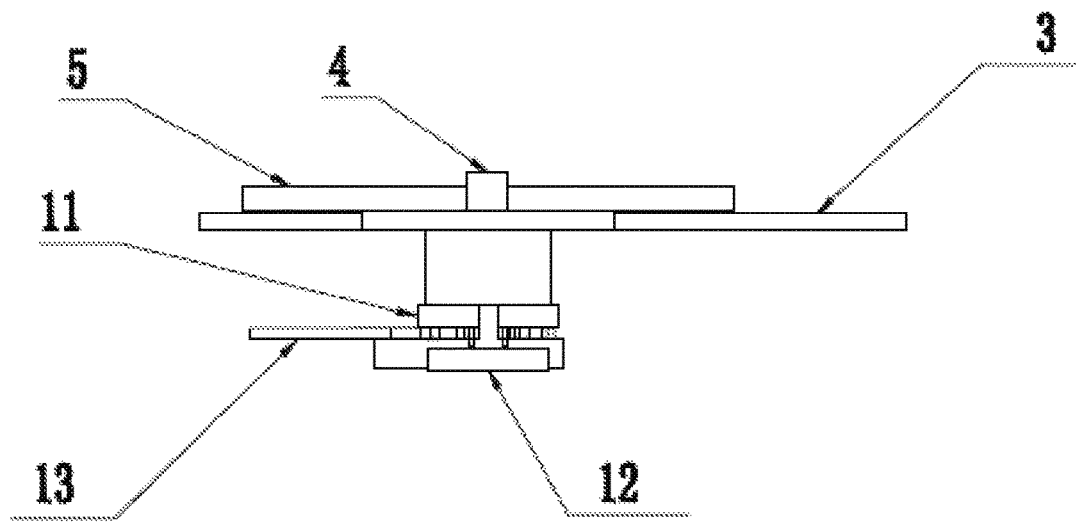
FIG. 8 is a front view showing a driver structure of a bio-chip detector according to one aspect the present disclosure.

In any of the preceding embodiments, a device disclosed herein can further comprise a driving device that comprises a rotor (e.g., 11 in FIG. 6 or FIG. 8) connected to the rotary shaft, a pushrod (e.g., 21 in FIG. 6) to rotate the rotor, a biasing member (e.g., 14 in FIG. 6) to return the pushrod to its original position, a rotor securing lever (e.g., 13 in FIG. 6 or FIG. 8) that fixes the rotor, and a spring (e.g., 15 in FIG. 6). In specific embodiments, the configurations of the various components are as follows.

In one aspect, the rotary shaft is connected to the rotor housed in the holding cavity by a coupling shaft (e.g., 16 in FIG. 5), and there are several protuberances around the periphery of the rotor, which are stressed subassembly to drive the rotor to rotate. As the subassembly to apply force, the pushrod is designed to fit the protuberances of rotor. The process of pushing the pushrod will lead to the rotation of the rotor, which further drives the rotation of the rotary shaft, which in turn leads to the rotation of the support frame. In one aspect, in order to facilitate manual operation, one end of the pushrod protrudes from the retention chamber. To drive the pushrod, an operator only needs to press the pushrod towards the retention chamber to operate the device. In another embodiment, the biasing member connected to the pushrod can reset the position of the pushrod in order to release the rotor. In one aspect, the biasing member causes the pushrod to re-protrude from the accommodating cavity for the convenience of operation. This is because, in one aspect, the pushrod and the rotor need to be separated after the operator presses the pushrod, so that the pushrod can inosculate with the next protuberance. In particular embodiments, the biasing member comprises a spring such as a return spring.

In a further aspect, the rotor securing lever is connected to the lower surface of the upper plate, and the rotor securing lever comprises a neck that can fit the protuberances of the rotor. The other end of the rotor securing lever that is not connected to the lower surface of the upper plate is connected to a spring (e.g., 15 in FIG. 6), for example, to one end of the spring. In one aspect, the other end of the spring is connected to the lower surface of the upper plate of the holding cavity. When the rotor is rotating, that is, when the neck and protuberance are separated, the spring strains the rotor securing lever to let the neck convex fit with the next protuberance with tensioning force. The cooperative operation of the rotor securing lever and the spring ensures the single-directional rotation of the rotor, which is similar to a ratchet pawl structure. An operator can set up the apparatus using a ratchet pawl structure as a reference.

In some embodiments, part of the biochip support frame can protrude from the closed carton of the first shell and the second shell, which means the radius of the biochip support frame can be larger than the distance between the rotary shaft and one fringe of the second shell. An operator can manually rotate the biochip support frame when needed. Other structures that can rotate the rotary shaft are within the scope of the present disclosure. In some embodiments, when a driving device is used, the biochip support frame can locate entirely within the closed carton formed by the first shell and the second shell to prevent the collision of the support frame with external substances or structures.

In a further embodiment, the pushrod comprises: a positioning rod (e.g., 20 in FIG. 6), a guiding rod (e.g., 10 in FIG. 6), and a button (e.g., 9 in FIG. 6). In one aspect, the positioning rod is fixed on the lower surface of the upper plate of the holding cavity. In another aspect, the guiding rod comprises a chute that fits with the positioning rod, which enables the guidance and control of the movement of the guiding rod by the positioning rod set on the upper plate. In order to drive the rotor, in one aspect, the guiding rod comprises a sharp-edged tip fitted to the protuberances of the rotor, so that its tip portion can collide with the protuberances to rotate the rotor by the movement of the guiding rod. In a further embodiment, the biasing member is connected to the guiding rod. In one aspect, when the force driving the guiding rod is released, the guiding rod is automatically detached from the rotor by the restoring force of the biasing member. To further facilitate operation, in one aspect, the pushrod also comprises a button, one end of which is connected to the guiding rod and the other end of which protrudes from the holding cavity. In one aspect, the operator only needs to press and release the button to step drive the rotor.

In one aspect, the driving device of the biochip detector disclosed herein comprises a damper (e.g., 12 in FIG. 7 or FIG. 8) connected to the rotor, which can buffer the rotation of the rotor to control or reduce its revolving speed.

In one aspect, the device disclosed herein further comprises a shielding plate (e.g., 19 in FIG. 1 or FIG. 2) disposed at the periphery of the light source. In one aspect, the shielding plate has the function of shielding the marginal rays of the light source to avoid the occurrence of the edge effect. In some embodiments, the diameter of the light spot formed through the shielding plate under the light source is larger than the diameter of the detecting zone.

In specific embodiments, the detector comprises a camera, or a camera system comprising a camera, an image processing unit, and/or a display unit. In some embodiments, the light source and the camera of the biochip detecting device are the only apparatuses that need power to function; therefore, the device can get its power supply from either a power socket or a common external battery. In specific embodiments, when the substance or target to be detected and/or analyzed is capable of emitting light itself, the light source may not be required for the detection or analysis.

In specific embodiments, a device disclosed herein can be used to detect and/or analyze a sample based on a chromogenic reaction. In specific embodiments, a device disclosed herein can be used to detect and/or analyze a sample based on color or color change, for example, the color characteristic value (CCV) of a sample or changes in the CCV of a sample due to the reaction. In one specific embodiment, one or more reagents for a reaction involving blood glucose are put in the biochip (for example, in a reaction unit of the biochip), and a chromogenic reaction may occur in the biochip after adding a sample. The color change of the reaction can then be detected. Then the operator can put the biochip on the support frame, close the first shell, connect the device to a power source, switch on the light source to turn on a LED lamp and camera, and rotate the biochip support frame that holds the biochip, while the camera monitors the biochip and its reaction unit through the detecting zone in real-time, records data, and performs analysis.

In some embodiments, the biochip detection device is used to determine the concentration of a nucleic acid in a sample. For example, light source of 260 nm wavelength can be obtained using an optical filter. Reagents associated with nucleic acids detection are placed in the biochip testing zone. After adding the sample to the biochip, an operator can fasten the biochip to the support frame, close the second shell, connect the device to a power source, switch on the light source to turn on the LED lamp and camera, and press the button on the lateral surface of the first shell to rotate the biochip. Every single click of the button leads to one biochip rotation that switches one testing zone to the next. In the meantime, the camera monitors the biochip through the detecting zone, records data, and performs analysis.

In one aspect, disclosed herein is a device comprising a first shell, and a second shell connected to the first shell, wherein the first and second shells are capable of engaging each other to form a substantially closed carton. In one aspect, the device further comprises a rotatable support frame located between the first and second shells. In one aspect, the rotatable support frame comprises a detecting zone that is capable of holding an object to be detected and/or analyzed. In any of the preceding embodiments, the device can further comprise a detector.

In any of the preceding embodiments, the first shell can comprise a holding cavity.

In any of the preceding embodiments, the holding cavity can comprise an upper plate facing the second shell.

In any of the preceding embodiments, the rotatable support frame can be disposed on the upper plate of the holding cavity of the first shell.

In any of the preceding embodiments, the upper plate can comprise a through-hole that is capable of aligning with the detecting zone of the rotatable support frame.

In any of the preceding embodiments, the device can further comprise a light source.

In any of the preceding embodiments, the light source can be disposed on the first shell or the second shell.

In any of the preceding embodiments, the light source and the detector can be disposed on opposite sides of the rotatable support frame.

In any of the preceding embodiments, the object can comprise a chip such as a biochip.

In any of the preceding embodiments, the device can be one for detecting and/or analyzing a chip such as a biochip.

In any of the preceding embodiments, the rotatable support frame can comprise a plurality of detecting zones each of which is capable of holding an object to be detected and/or analyzed.

In any of the preceding embodiments, the device can further comprise an output unit for outputting a result of the detection and/or analysis.

In any of the preceding embodiments, the output unit can be disposed on the first shell, such as in a holding cavity of the first shell.

In any of the preceding embodiments, the light source can be disposed on the second shell, and the detector can be disposed in the holding cavity of the first shell and aligns with the through-hole.

In any of the preceding embodiments, the detector, the light source, the detecting zone, and the through-hole can be collinear when the first and second shells engage each other to form a substantially closed carton.

In any of the preceding embodiments, the device can further comprise one or more macro lenses.

In any of the preceding embodiments, the one or more macro lenses can be disposed in the holding cavity of the first shell.

In any of the preceding embodiments, the one or more macro lenses can be disposed between the through-hole and the detector.

In any of the preceding embodiments, the one or more macro lenses can be collinear with the through-hole and the detector.

In any of the preceding embodiments, the device can further comprise one or more optical filters disposed between the through-hole and the one or more macro lenses.

In any of the preceding embodiments, the device can further comprise a rotary shaft disposed on or connected to the upper plate of the holding cavity of the first shell.

In any of the preceding embodiments, the rotary shaft can be disposed on or connected to the support frame.

In any of the preceding embodiments, the device can further comprise a driving unit that is capable of rotating the rotary shaft.

In any of the preceding embodiments, the driving unit can be disposed in the holding cavity.

In any of the preceding embodiments, the driving unit can comprise a rotor connected to the rotary shaft, which rotor comprises a plurality of protuberances around the periphery of the rotor. In any of the preceding embodiments, the driving unit can further comprise a pushrod that is capable of applying a force to drive the rotation of the rotor, which pushrod is configured to fit the protuberances of the rotor and protrude from the holding cavity. In any of the preceding embodiments, the driving unit can further comprise a biasing member connected to the pushrod that is capable of resetting the position of the pushrod to release the rotor. In any of the preceding embodiments, the driving unit can further comprise a rotor securing lever that is connected to the lower surface of the upper plate of the holding cavity, which rotor securing lever comprises a neck that is capable of fitting the protuberances of the rotor to make the rotor spin in a single direction. In any of the preceding embodiments, the driving unit can further comprise a spring connected to the rotor securing lever at one end and to the lower surface of the upper plate of the holding cavity at the other end.

In any of the preceding embodiments, the pushrod can comprise a positioning rod disposed on the lower surface of the upper plate of the holding cavity. In any of the preceding embodiments, the pushrod can further comprise a guiding rod comprising a sharp-edged tip capable of fittingly engage the protuberances of the rotor. In any of the preceding embodiments, the pushrod can comprise a chute capable of fittingly engage the positioning rod, which guiding rod is connected to the biasing member. In any of the preceding embodiments, the pushrod can comprise a button connected to the guiding rod at one end, with the other end protruding from the holding cavity.

In any of the preceding embodiments, the driving unit can further comprise a damper connected to the rotor.

In any of the preceding embodiments, the device can further comprise a light source and a shielding plate disposed at the periphery of the light source.

In some aspects, provided herein is a method of detecting and/or analyzing an object. In some embodiments, the method comprises placing the object in the detecting zone of the device of any of the preceding embodiments.

Further embodiments are provided herein to illustrate the present disclosure.

Embodiment 1

A biochip detecting device that features:

Two connected shells: First Shell [2] with a holding cavity and Second Shell [1], and the upper plate of the holding cavity [3] faces Second Shell [1];

A rotatable support frame of biochip [5] possessing a detecting zone that holds biochips is set on the upper plate, and the upper plate [3] also has a though-hole [8] that can face the detecting zone;

A light source [6] that provides lighting for biochips that is set either in First Shell [2] or Second Shell [1];

A biochip detector [7] that detects the testing zone of the biochip is placed in either First Shell [2] or Second Shell [1] depending on the side on which the light source is located. Simultaneously, the detector [7] and the light source [6] are set on opposite sides of the support frame [5]; and A device which outputs the detection results fixed in the holding cavity of First Shell [2].

Embodiment 2

A biochip detecting device according to Embodiment 1, wherein the light source [6] is placed on Second Shell [1], and the biochip detector [7] is placed in the holding cavity of First Shell [2] facing the though-hole [8].

Embodiment 3

A biochip detecting device according to Embodiment 2, wherein the device further comprises macro lenses [17] that are fixed in the holding cavity of the First Shell [2], and the macro lenses [17] face the through-hole [8], set between the through-hole [8] and the detector [7].

Embodiment 4

A biochip detecting device according to Embodiment 3, wherein the optical filter [18] is set between the through-hole [8] and the macro lenses [17].

Embodiment 5

A biochip detecting device according to Embodiment 1, wherein the rotary shaft [4] is set on the upper plate [3] of the holding cavity of the First Shell [2], and the biochip support frame [5] is fixed on the rotary shaft [4].

Embodiment 6

A biochip detecting device according to Embodiment 5, wherein the driving device that is used to rotate the rotary shaft [4] is fixed in the holding cavity.

Embodiment 7

A biochip detecting device according to Embodiment 6, wherein the driving device comprises:

A rotor [11] that is connected to the rotary shaft [4], and there are multiple protuberances around the periphery of rotor [11];

As the subassembly to apply force to drive the rotation of the rotor [11], a pushrod [21] that is designed to fit the protuberances of rotor [11], and the pushrod [21] protrudes from the holding cavity;

A biasing member [14] connected to the pushrod [21] that resets the position of the pushrod to release the rotor [11];

A rotor securing lever [13] that is connected to the lower surface of the upper plate of the holding cavity, and this lever [13] has a neck that can fit the protuberances of rotor [11] to make the rotor spin in a single direction; and A spring [15] that is connected to the rotor securing lever [13] at its one end and the lower surface of the upper plate of the holding cavity at the other end.

Embodiment 8

A biochip detecting device according to Embodiment 7, wherein the pushrod [21] comprises:

A positioning rod [20] that is fixed on the lower surface of the upper plate of the holding cavity;

A guiding rod [10] with a sharp-edged tip fitted to the protuberances of the rotor that has a chute that fits with the positioning rod [20], and this guiding rod [10] is connected to the biasing member [14]; and A button [9] that is connected to the guiding rod [10] at its one end, the other end of which protrudes from the holding cavity.

Embodiment 9

A biochip detecting device according to Embodiment 7, wherein the driving device of the biochip detector further comprises a damper [12] connected to the rotor [11].

Embodiment 10

A biochip detecting device according to any one of Embodiments 1-9, wherein the biochip detector further comprises a shielding plate [19] disposed at the periphery of the light source [6].

Various embodiments in the device of the present disclosure are described in a progressive manner. Differences between various embodiments are emphasized in their specifications, while their common structures can be referred from the description.

The invention claimed is:

1. A device, comprising:
a first shell;
a second shell connected to the first shell, wherein the first and second shells are configured to engage with each other to form a substantially closed carton;
a rotatable support frame located between the first and second shells, wherein the rotatable support frame comprises a detecting zone configured to hold an object to be detected and/or analyzed; and
a detector;
further comprising a light source, wherein, the light source is disposed on the first shell or the second shell, and wherein the light source and the detector are disposed on opposite sides of the rotatable support frame.

2. The device of claim 1, wherein the first shell comprises a holding cavity.

3. The device of claim 2, wherein the holding cavity comprises an upper plate facing the second shell.

4. The device of claim 3, wherein the rotatable support frame is disposed on the upper plate of the holding cavity of the first shell.

5. The device of claim 3, wherein the upper plate comprises a through-hole that is capable of aligning with the detecting zone of the rotatable support frame.

6. The device of claim 1, wherein the object comprises a chip such as a biochip.

7. The device of claim 1, wherein the device is for detecting and/or analyzing a chip such as a biochip.

8. The device of claim 1, wherein the rotatable support frame comprises a plurality of detecting zones each of which is capable of holding an object to be detected and/or analyzed.

9. The device of claim 1, further comprising an output unit for outputting a result of the detection and/or analysis.

10. The device of claim 9, wherein the output unit is disposed on the first shell, such as in a holding cavity of the first shell.

11. The device of claim 1, wherein the light source is disposed on the second shell.

12. The device of claim 11, wherein the detector is disposed in the holding cavity of the first shell and aligns with the through-hole.

13. The device of claim 12, wherein the detector, the light source, the detecting zone, and the through-hole are collinear when the first and second shells engage each other to form a substantially closed carton.

14. The device of claim 1, further comprising one or more macro lenses.

15. The device of claim 1, further comprising one or more macro lenses.

16. The device of claim 15, wherein the one or more macro lenses are disposed in the holding cavity of the first shell.

17. The device of claim 15, wherein the one or more macro lenses are disposed between the through-hole and the detector.

18. The device of claim 15, wherein the one or more macro lenses are collinear with the through-hole and the detector.

19. The device of claim 15, further comprising one or more optical filters disposed between the through-hole and the one or more macro lenses.

20. The device of claim 1, further comprising a rotary shaft disposed on or connected to the upper plate of the holding cavity of the first shell.

21. The device of claim 20, wherein the rotary shaft is disposed on or connected to the support frame.

22. The device of claim 21, further comprising a driving unit that is capable of rotating the rotary shaft.

23. The device of claim 22, wherein the driving unit is disposed in the holding cavity.

24. A device, comprising:
a first shell;
a second shell connected to the first shell, wherein the first and second shells are capable of engaging each other to form a substantially closed carton;
a rotatable support frame located between the first and second shells, wherein the rotatable support frame comprises a detecting zone that is capable of holding an object to be detected and/or analyzed;
a detector;
a light source;
a rotary shaft disposed on or connected to the upper plate of the holding cavity of the first shell, wherein the rotary shaft is disposed on or connected to the support frame;
a driving unit that is capable of rotating the rotary shaft, wherein the driving unit is disposed in the holding cavity;
a rotor connected to the rotary shaft, which rotor comprises a plurality of protuberances around the periphery of the rotor;
a pushrod that is capable of applying a force to drive the rotation of the rotor, which pushrod is configured to fit the protuberances of the rotor and protrude from the holding cavity;
a biasing member connected to the pushrod that is capable of resetting the position of the pushrod to release the rotor;
a rotor securing lever that is connected to the lower surface of the upper plate of the holding cavity, which rotor securing lever comprises a neck that is capable of fitting the protuberances of the rotor to make the rotor spin in a single direction; and
a spring connected to the rotor securing lever at one end and to the lower surface of the upper plate of the holding cavity at the other end.

25. The device of claim 24, wherein the pushrod comprises:
a positioning rod disposed on the lower surface of the upper plate of the holding cavity;
a guiding rod comprising a sharp-edged tip capable of fittingly engage the protuberances of the rotor, and a chute capable of fittingly engage the positioning rod, which guiding rod is connected to the biasing member; and
a button connected to the guiding rod at one end, with the other end protruding from the holding cavity.

26. The device of claim 24, wherein the driving unit further comprises a damper connected to the rotor.

27. The device of claim 1, further comprising a light source and a shielding plate disposed at the periphery of the light source.

28. A method of detecting and/or analyzing an object, comprising placing the object in the detecting zone of the device of claim 1.

* * * * *